United States Patent
McKee (10) Patent No.: US 9,671,402 B2
(45) Date of Patent: Jun. 6, 2017

(54) LATERAL FLOW BLOTTING ASSAY

(71) Applicant: Bio-Rad Laboratories, Inc., Hercules, CA (US)

(72) Inventor: Clayton McKee, Davis, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/634,209

(22) Filed: Feb. 27, 2015

(65) Prior Publication Data

US 2015/0241425 A1 Aug. 27, 2015

Related U.S. Application Data

(60) Provisional application No. 61/945,376, filed on Feb. 27, 2014.

(51) Int. Cl.
*G01N 33/558* (2006.01)

(52) U.S. Cl.
CPC .................................. *G01N 33/558* (2013.01)

(58) Field of Classification Search
None
See application file for complete search history.

(56) References Cited

U.S. PATENT DOCUMENTS

| 4,632,901 A | 12/1986 | Valkirs et al. |
| 5,957,593 A | 9/1999 | Kroon |
| 8,206,664 B2 | 6/2012 | Lin |
| 2006/0160078 A1 | 7/2006 | Cardy et al. |
| 2010/0184687 A1 | 7/2010 | Staby et al. |
| 2010/0239459 A1 | 9/2010 | Alajem et al. |
| 2011/0165081 A1 | 7/2011 | Schulke et al. |
| 2013/0131323 A1 | 5/2013 | Van Alstine et al. |
| 2013/0164193 A1 | 6/2013 | Semenov et al. |
| 2013/0280698 A1* | 10/2013 | Propper ............. G01N 33/5302 435/5 |
| 2014/0027284 A1 | 1/2014 | McKee et al. |

FOREIGN PATENT DOCUMENTS

WO 95/52934 A 10/1999

OTHER PUBLICATIONS

Ge Healthcare. "Principles of ion exchange", *Ion Exchange Chromotography and Chromatography.*, pp. 1-185. http://www.gelifesciences.com/gehcls_images/GELS/Related%20Content/Files/1314823637792/litdoc11000421_20140926235100.pdf.

Moores et al., "Sequence Dependence of Protein Isoprenylation", The *Journal of Biological Chemistry*, vol. 266, No. 22, pp. 14603-14610 (1991).

International Search Report and Written Opinion dated Oct. 15, 2014 for International Patent Application No. PCT/US2014/048072, 10 pages.

Chothia et al., "Canonical Structures for the Hypervariable Regions of Immunoglobulins", *J. Mol. Biol.*, 196, 901-917 (1987).

Chothia et al., "Structural Repertoire of the Human VH Segments", *J. Mol. Biol.*, vol. 227, pp. 799-817 (1992).

Ruiz et al., "IMGT, the international ImMunoGeneTics database", *Nucleic Acids Res.*, vol. 28, pp. 219-221 (2000).

(Continued)

*Primary Examiner* — Rebecca Martinez
(74) *Attorney, Agent, or Firm* — Kilpatrick Townsend and Stockton LLP (57) ABSTRACT

Methods, compositions, and kits for performing analyte detection in a lateral flow assay.

18 Claims, 3 Drawing Sheets

(56) References Cited

OTHER PUBLICATIONS

Lefranc, "IMGT, the international ImMunoGeneTics database", *Nucleic Acids Res.*, vol., 29, No. 1, pp. 207-209 (2001).
Martin et al, "Modeling antibody hypervariable loops: A combined algorithm", *Proc. Natl Acad. Sci. USA*, vol. 86, pp. 9268-9272 (1989).
Jallerat & Thom, Filter Membranes and Bioseparation Equipment and Supplies, IVD Technology (Oct. 2004).
Lu et al., "Rapid prototyping of paper-based microfluidics with wax for low-cost, portable bioassay," *Electrophoresis*, vol. 30, 1497-1500 (2009).
Carrilho et al., "Understanding Wax Printing: A Simple Micropatterning Process for Paper-Based Microfluidics," *Anal. Chem.*, vol. 81, No. 16, pp. 7091-7095 (2009).
Shiroguchi et al. "Digital RNA sequencing minimizes sequence-dependent bias and amplification noise with optimized single-molecule barcodes", *PNAS*, vol. 109, No. 4, pp. 1347-1352 (2012).
Smith et al., "Highly-multiplexed barcode sequencing: an efficient method for parallel analysis of pooled samples", Nucleic Acids Research, vol. 38, No. 13, pp. e142, 7 pages (2010).
Kolb et al., "Click Chemistry: Diverse Chemical Function from a Few Good Reactions", *Agnew Chem*, vol. 40, pp. 2004-2021 (2001).
Goyal et al., "LEA proteins prevent protein aggregation due to water stress", *Biochem J.*, vol. 388 (pt.1), pp. 151-157 (2005).
U.S. Appl. No. 13/950,590, filed Jul. 25, 2013.
International Search Report and Written Opinion dated Jun. 3, 2015 for International Patent Application No. PCT/US2015/018165.

\* cited by examiner

LATERAL FLOW BLOTTING ASSAY

CROSS-REFERENCE TO RELATED APPLICATION

This application claims priority to U.S. Provisional Application No. 61/945,376, filed Feb. 27, 2014, the contents of which are hereby incorporated in the entirety for all purposes.

BACKGROUND OF THE INVENTION

Methods for detection of immobilized analytes are commonly employed in the biological sciences. For example, traditional blotting (e.g., Southern, northern, western, far western, eastern, vacuum, middle eastern, eastern-western, and far-eastern blotting, etc.) can be used to detect analytes immobilized on a substrate or membrane or in a matrix (e.g., in agarose or acrylamide). In general, such blotting techniques involve immobilization of the analyte(s) to be detected and contacting the analyte(s) with a binding reagent (e.g., an antibody). Blotting also usually involves multiple washing steps and/or blocking steps between immobilization and final detection. Such washing and blocking steps consume a practitioner's limited time and/or reagents and are a frequent source of error and irreproducibility.

BRIEF SUMMARY OF THE INVENTION

The present invention provides improved methods, compositions, and kits for detection of immobilized analytes.

In some embodiments, the present invention provides a porous substrate having a length and a width and comprising a reagent reservoir region and a lateral flow region, said reagent reservoir region comprising or bordered by an impermeable or hydrophobic barrier, said impermeable or hydrophobic barrier substantially blocking flow of a liquid from the reagent reservoir region into the lateral flow region until lateral flow is initiated. In some cases, the lateral flow region is configured to wick one or more binding reagents from the reagent reservoir and along the length of the lateral flow region after contacting the lateral flow region with the reagent reservoir region.

In some embodiments, the porous substrate further comprises a folding region, wherein the folding region is positioned to allow initiating of lateral flow by folding the porous substrate at the folding region, wherein folding the porous substrate at the folding region contacts at least a portion of the reagent reservoir region to at least a portion of the lateral flow region.

In some aspects, said reagent reservoir region comprises at least a first reagent reservoir sub-region and a second reagent reservoir sub-region, wherein the first and second reagent reservoir sub-regions are not in fluid communication; and said lateral flow region comprises at least a first lateral flow sub-region and a second lateral flow sub-region, wherein said first and second lateral flow sub-regions are not in fluid communication.

In some cases, the first reagent reservoir sub-region is separated from the second reagent reservoir sub-region by a hydrophobic or impermeable barrier. In some cases, the first lateral flow sub-region is separated from the second lateral flow sub-region by a hydrophobic or impermeable barrier. In some cases, each reagent reservoir sub-region is configured such that each sub-region can be separately contacted to a corresponding lateral flow sub-region. For example, one or more reagent reservoir sub-regions can be individually and independently folded at the folding reagent to contact a corresponding lateral flow sub-region.

In some embodiments, the lateral flow region and/or the reagent reservoir region comprises a capillary flow matrix. In some aspects, at least a portion of the porous substrate, e.g., at least a portion of the capillary flow matrix, is coupled to an impermeable or hydrophobic backing. The capillary flow matrix can comprise cellulose or glass fibers.

In some embodiments, the folding region comprises a visual marker, a pleat, or a crease. In some cases, the folding region extends across the width of the porous substrate. In some cases, the lateral flow region is configured to wick one or more binding reagents from the reagent reservoir and along the length of the lateral flow region after folding the folding region.

In some embodiments, at least a portion of the porous substrate is substantially compressible. For example, in some cases, at least a portion of the lateral flow region is substantially compressible. As another example, at least a portion of the reagent reservoir region is substantially compressible.

In some embodiments, the reagent reservoir region comprises a first primary binding reagent. The reagent reservoir region can also comprise a second primary binding reagent. In some aspects, the first and second primary binding reagents of the reagent reservoir region are separated by an impermeable or hydrophobic barrier.

In any of the preceding aspects, embodiments, or cases, the reagent reservoir region and/or the lateral flow region of the porous substrate can contain a protein aggregation modifying agent.

In some embodiments, the present invention provides a method for performing a lateral flow assay comprising: —providing a porous substrate comprising a lateral flow region; —placing the porous substrate in intimate contact with a membrane comprising a plurality of immobilized analytes; and —contacting the lateral flow region with a reagent reservoir region comprising a primary binding reagent, thereby causing at least a portion of the primary binding reagent to wick into the lateral flow region, wherein causing at least a portion of the primary binding reagent to wick into the lateral flow region initiates lateral flow of the primary binding reagent through at least a portion of the lateral flow region, thereby contacting at least a portion of the primary binding reagent to the membrane comprising a plurality of immobilized analytes.

In some aspects, the method further comprises initiating lateral flow of a wash solution through at least a portion of the lateral flow region. In some aspects, the method further comprises initiating lateral flow of a solution containing a secondary binding reagent through at least a portion of the lateral flow region. In some cases, initiating lateral flow of a wash solution can be performed after initiating lateral flow of the solution containing a secondary binding reagent through at least a portion of the lateral flow region. In some cases, initiating lateral flow of a wash solution can be performed after lateral flow of the primary binding reagent.

In some aspects, the porous substrate comprising a lateral flow region further comprises the reagent reservoir region, and the reagent reservoir region is separated from the lateral flow region by (i) an impermeable or hydrophobic barrier and (ii) a folding region. In some cases, wherein the folding region extends across the width of the porous substrate. In some cases, contacting the porous substrate with the reagent reservoir region comprising the primary binding reagent comprises folding the porous substrate at the folding region. In some cases, the lateral flow region is configured to wick one or more binding reagents from the reagent reservoir and along the length of the lateral flow region after folding the folding region. The folding region can comprise a visual marker, a pleat, or a crease. In some cases, at least a portion of the lateral flow region, at least a portion of the reagent reservoir region, or at least a portion of the porous substrate is substantially compressible.

In some embodiments, the reagent reservoir region comprises at least a first reagent reservoir sub-region and a second reagent reservoir sub-region, wherein the first and second reagent reservoir sub-regions are not in fluid communication; and said lateral flow region comprises at least a first lateral flow sub-region and a second lateral flow sub-region, wherein said first and second lateral flow sub-regions are not in fluid communication. In some aspects, the first and second reagent reservoir sub-regions can be separately contacted with the first and second lateral flow sub-regions respectively. For example, one or more reagent reservoir sub-regions can each be independently folded at the folding reagent to each contact a corresponding lateral flow sub-region.

In some cases, the first reagent reservoir sub-region is separated from the second reagent reservoir sub-region by a hydrophobic or impermeable barrier, and the first lateral flow sub-region is separated from the second lateral flow sub-region by a hydrophobic or impermeable barrier.

In some embodiments, the first reagent reservoir sub-region comprises a first primary binding reagent and the second reagent reservoir sub-region comprises a second primary binding reagent. In some embodiments, the reagent reservoir region comprises a protein aggregation modifying agent.

In some embodiments of the method, the porous substrate, at least a portion of the porous substrate, the reagent reservoir region, at least a portion of the reagent reservoir region, the lateral flow region, and/or at least a portion of the lateral flow region comprises a capillary flow matrix. For example, the capillary flow matrix can comprise cellulose or glass fibers. In some embodiments of the method, the porous substrate, at least a portion of the porous substrate, the reagent reservoir region, at least a portion of the reagent reservoir region, the lateral flow region, and/or at least a portion of the lateral flow region is coupled to an impermeable or hydrophobic backing.

In some embodiments, the present invention provides a kit comprising at least one (e.g., 1, 2, 3, 4, 5, 6, 7, 8, 9, 10, or more) of any of the foregoing porous substrates. In some cases, the kit further comprises a first and a second primary binding reagent. In some cases, the kit further comprises a container having a protein aggregation modifying agent. In some cases, the protein aggregation modifying agent is a cyclodextrin.

BRIEF DESCRIPTION OF THE DRAWINGS

In step 1, binding reagents (e.g., antibodies) are loaded into self-contained reagent reservoir sub-regions demarcated by hydrophobic barriers. In step 2, the porous substrate is folded to cause contact between the reagent reservoir and lateral flow region. Wicking causes lateral flow of the antibodies through the porous substrate, thereby contacting the antibodies to the proteins bound to the western blot membrane. The immobilized proteins indicated by the circles are detected and identified by their binding to a binding reagent. The location of the detected analyte on the membrane can provide further information regarding the identity of the analyte.

DETAILED DESCRIPTION OF THE INVENTION

I. Definitions

The term "analyte" refers to a biological molecule, e.g., a protein, nucleic acid, polysaccharide, lipid, antigen, growth factor, hapten, etc., or a portion thereof. Analytes can be irreversibly immobilized on a surface, such as a membrane and detected as described herein.

The term "immobilized" as used herein refers to reversibly and irreversibly immobilized molecules (e.g., binding reagents or analytes). Reversibly immobilized molecules are immobilized in a manner that allows the molecules, or a portion thereof (e.g., at least 25%, 50%, 60%, 75%, 80% or more of the molecules), to be removed from their immobilized location without substantial denaturation or aggregation. For example, a molecule can be reversibly immobilized in or on a porous substrate by contacting a solution containing the molecule with the porous substrate, thereby soaking up the solution and reversibly immobilizing the molecule. The reversibly immobilized molecule can then be removed by wicking the solution from the porous substrate, or from one region of the porous substrate to another. In some cases, a molecule can be reversibly immobilized on a porous substrate by contacting a solution containing the molecule with the porous substrate, thereby soaking up the solution, and then drying the solution containing porous substrate. The reversibly immobilized molecule can then be removed by contacting the porous substrate with another solution of the same or a different composition, thereby solubilizing the reversibly immobilized molecule, and then wicking the solution from the porous substrate, or from one region of the porous substrate to another.

Irreversibly immobilized molecules (e.g., binding reagents or analytes) are immobilized such that they are not removed, or not substantially removed, from their location under mild conditions (e.g., pH between about 4-9, temperature of between about 4-65° C.). Exemplary irreversibly immobilized molecules include protein analytes bound to a nitrocellulose or polyvinylidene fluoride membrane by standard blotting techniques (e.g., electroblotting).

The term "binding reagent" refers to a reagent that specifically binds to a molecule such as an analyte. A wide variety of binding reagents are known in the art, including antibodies, aptamers, affimers, lipocalins (e.g., anticalins), thioredoxin A, bilin binding protein, or proteins containing an ankyrin repeat, the Z domain of staphylococcal protein A, or a fibronectin type III domain.

The term "specifically bind" refers to a molecule (e.g., binding reagent such as an antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, 100-fold, or 1000-fold or more greater affinity.

The term "antibody" refers to a polypeptide comprising a framework region from an immunoglobulin gene, or fragments thereof, that specifically bind and recognize an antigen, e.g., a particular analyte. Typically, the "variable region" contains the antigen-binding region of the antibody (or its functional equivalent) and is most critical in specificity and affinity of binding. See Paul, *Fundamental Immunology* (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

An "isotype" is a class of antibodies defined by the heavy chain constant region. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

A "monoclonal antibody" refers to a clonal preparation of antibodies with a single binding specificity and affinity for a given epitope on an antigen. A "polyclonal antibody" refers to a preparation of antibodies raised against a single antigen, but with different binding specificities and affinities.

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, (1987) *J. Mol. Biol.* 196, 901-917; Chothia et al. (1989) Nature 342, 877-883; Chothia et al. (1992) J. Mol. Biol. 227, 799-817; Al-Lazikani et al., *J. Mol. Biol* 1997, 273(4)). Definitions of antigen combining sites are also described in the following: Ruiz et al. *Nucleic Acids Res.*, 28, 219-221 (2000); and Lefranc *Nucleic Acids Res.* January 1; 29(1):207-9 (2001); MacCallum et al., *J. Mol. Biol.*, 262: 732-745 (1996); and Martin et al, *Proc. Natl Acad. Sci. USA*, 86, 9268-9272 (1989); Martin, et al, *Methods Enzymol.*, 203: 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

A "chimeric antibody" is an antibody molecule in which (a) the constant region, or a portion thereof, is altered, replaced or exchanged so that the antigen binding site (variable region, CDR, or portion thereof) is linked to a constant region of a different or altered class, effector function and/or species, or an entirely different molecule which confers new properties to the chimeric antibody (e.g., an enzyme, toxin, hormone, growth factor, drug, etc.); or (b) the variable region, or a portion thereof, is altered, replaced or exchanged with a variable region having a different or altered antigen specificity (e.g., CDR and framework regions from different species).

The antibody binds to an "epitope" on the antigen. The epitope is the specific antibody binding interaction site on the antigen, and can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous or conformational epitope). The same is true for other types of target molecules that form three-dimensional structures.

II. Introduction

Compositions, methods, and kits described herein can be useful for detecting analytes bound to a membrane. For example, described herein is a porous substrate. The porous substrate can be placed in intimate contact with a membrane containing bound analytes. Lateral flow of one or more binding reagents through the region of the porous substrate in intimate contact with the membrane can allow the one or more binding reagents to bind, and thereby detect, one or more membrane-bound analytes. The porous substrate can be divided into two or more sub-regions by impermeable or hydrophobic barriers such that detection of one or more analytes in one sub-region does not confound detection in another sub-region. Thus, multiplex detection can be performed using the compositions, methods, and kits described herein. In some cases, the porous substrate is configured for use in a sequential lateral flow device.

III. Compositions

A. Porous Substrate

A porous substrate can useful for storage of one or more binding reagents. A porous substrate can also be useful for detection of one or more immobilized analytes. The porous substrate has a width, a length, and a height (e.g., a thickness). The substrate can be any size and shape. In certain embodiments, the porous substrate is planar, e.g., the porous substrate can approximate or be a rectangular plane. In some cases, the length and the width of the porous substrate are at least about 2-fold, 5-fold, 10-fold, 100-fold or more larger than the height (i.e., thickness). In some embodiments, the porous substrate is sized for use in a blotting apparatus. For example, the porous substrate can be sized to transfer reagents through at least a portion of the porous substrate, and thereby contact the reagents to a blotting membrane having one or more analytes irreversibly immobilized thereon. In some embodiments, the porous substrate has an impermeable, or substantially impermeable backing Exemplary sizes for porous substrates include, without limitation, porous substrates that are at least about 0.25 cm, 0.5 cm, 1 cm, 2 cm, 3 cm, 4 cm, 5 cm, 6 cm, 7 cm, 8 cm, 10 cm, 12 cm, 15 cm, 20 cm, 30 cm or more in at least one dimension. Exemplary sizes of rectangular planar porous substrates include porous substrates that are about 1 cm×1 cm, 7×8.4 cm, 8.5×13.5 cm, 10 cm×15 cm, or 25×28 cm in length and width respectively. Exemplary sizes further include 8.5 cm×9 cm, 7 cm×9 cm, 8 cm×10.7 cm, 10 cm×10 cm, 7 cm×8.5 cm, 8.3 cm×7.3 cm, 8 cm×8 cm, 8.3 cm×13 cm, 10.8 cm×13.5 cm. In some embodiments, the porous substrate is 18 cm in length by 10 cm in width. In some cases, the porous substrate is 18±0.5, 1, 2, or 3 cm in length by 10±0.5, 1, 2, or 3 cm in width.

In some embodiments, the porous substrate is configured to have a high solution capacity and lateral flow rate. In some cases, the high solution capacity and lateral flow rate are provided by having a porous substrate with substantial height (e.g., thickness). In some cases, the porous substrate is about 10, 9, 8, 7, 6, 5, 4, 3, 2, 1, 0.75, 0.5, or about 0.2 mm thick. In some cases, the porous substrate is between about 0.05 mm and about 0.5 mm thick.

Porous substrates generally have a large surface area due to the presence of a plurality of pores. The large surface area can increase the loading capacity of the porous substrate for one or more reagents or one or more solutions containing a reagent. In some embodiments, the porous substrate, or a portion thereof, such as a lateral flow region or a reagent reservoir region, has a large surface area as compared to a nonporous substrate of the same material and size. For example, the porous substrate can have at least about a 2, 3, 4, 5, 6, 7, 8, 9, 10, 15, 20, 25, 30, 40, 50, 100, 200, 300, 500, 1000-fold or more increased surface area as compared to a nonporous substrate of the same material and size. In some embodiments, the porous substrate, or a portion thereof, such as a lateral flow region or a reagent reservoir region, has a large specific surface area. For example, the porous substrate can have a specific surface area of at least about 0.1 $m^2/g$, 0.5 $m^2/g$, 1 $m^2/g$, 10 $m^2/g$, or more as measured by standard techniques.

In some embodiments, the porous substrate, or a portion thereof, such as a lateral flow region or a reagent reservoir region, possesses a high specific binding capacity for a binding reagent (e.g., antibody). For example, in some cases, the porous substrate can reversibly immobilize at least about 0.1 mg, 0.5 mg, 1 mg, 5 mg, 10 mg, 15 mg, 20 mg, 40 mg, 60 mg, 100 mg, or more binding reagent for every mg of substrate material.

In some embodiments, the porous substrate can have a particular pore size, a particular average pore size, or a particular pore size range. For example, the porous substrate can contain 0.1 μm pores, 0.2 μm pores, 0.45 μm pores, or 1, 2, 4, 5, 6, 7, 8, 10, 15, 20 μm pores, or pores larger than about 20 μm. As another example, the porous substrate can contain pores that average 0.1, 0.2, 0.45, 1, 2, 4, 5, 6, 7, 8, 10, 15, or 20 μm, or more in size. As another example, the porous substrate can contain pores that range about 0.1-8 μm, 0.2-8 μm, 0.45-8 μm, 1-8 μm, 0.1-4 μm, 0.1-2 μm, 0.1-1 μm, 0.1-0.45 μm, 0.2-8 μm, 0.2-4 μm, 0.2-2 μm, 0.2-1 μm, 0.2-0.45 μm, 0.45-8 μm, 0.45-4 μm, 0.45-2 μm, 0.45-1 μm in size. In some cases, the porous substrate can contain pores that are less than about 20 μm in size. For example, the porous substrate can be composed of a material in which at least about 50%, 60%, 70%, 80%, 90% or more of the pores are less than about 20, 15, 10, or 5 μm in size. In some cases, the pores are large enough to contain one or more proteins of average size (e.g., about 1 nm). For example, the pores can be at least 1 nm in size, at least 5 nm in size, at least 10, 100, or 500 nm in size. Alternatively, at least 50%, 60%, 70%, 80%, 90% or more of the pores can be more than 1, 5, 10, 50, 100, or 500 nm in size. As used herein, pore size can be measured as a radius or a diameter. In some cases, the porous substrate contains porous polyethylene, such as porous polyethylene having a pore size between 0.2 and 20 microns, or between 1 and 12 microns. The porous substrate can have a different pore size in different regions of the substrate. For example, a reagent reservoir region can have a pore size or pore size range, and a lateral flow region can have a different pore size or pore size range.

The substrate can be treated or functionalized to minimize non-specific reagent binding, increase lateral flow, increase wicking, or to reduce protein aggregation. For example, the substrate, or a portion thereof, can be treated to alter the hydrophilicity or alter the hydrophobicity of the treated area. In some cases, altering the hydrophilicity or hydrophobicity of a porous substrate can increase binding reagent loading, decrease binding reagent aggregation or denaturation, create mask regions in which binding reagent is excluded from or not loaded, or direct flow of binding reagents when the substrate is wet. In some cases, the porous substrate contains a protein aggregation modifying agent as described herein.

The porous substrate can be marked or annotated such that the origin, composition, or location of a reversibly immobilized binding reagent (e.g., a primary antibody) is recorded. For example, one or more regions containing reversibly immobilized binding reagent(s) can be visually discernible, such that one of skill in the art can determine the location of the reversibly immobilized binding reagent. In some cases, the name of the binding reagent (e.g., antiphospho PIK3), identity (e.g., catalog number), amount, lot number, etc. can be printed, stamped, or otherwise indicated on a portion of the porous substrate. In some cases, the substrate is marked or annotated such that the proper orientation for use in a blotting device, e.g., in a sequential lateral flow capillary device, is discernible.

Porous substrates can include, but are not limited to, polymer containing substrates. The polymer can be in the form of polymer beads, a polymer membrane, or a polymer monolith. In some cases, the polymer is cellulose. Cellulose containing substrates include paper, cloth, woven, or non-woven cellulose substrates. Cloth substrates include those containing a natural cellulose fiber such as cotton or wool. Paper substrates include those containing natural cellulose fiber (e.g., cellulose or regenerated cellulose) and those containing cellulose fiber derivatives including, but not limited to cellulose esters (e.g., nitrocellulose, cellulose acetate, cellulose triacetate, cellulose proprionate, cellulose acetate propionate, cellulose acetate butyrate, and cellulose sulfate) and cellulose ethers (e.g., methylcellulose, ethylcellulose, ethyl methyl cellulose, hydroxyethyl cellulose, hydroxyethyl methyl cellulose, hydroxypropyl methyl cellulose, ethyl hydroxyethyl cellulose, and carboxymethyl cellulose). In some cases, the cellulose substrate contains rayon. In some cases, the substrate is paper, such as a variety of WHATMAN® paper.

Porous substrates can also include, but are not limited to, substrates that contain a sintered material. For example, the substrate can contain a sintered glass, a sintered polymer, or sintered metal, or a combination thereof. In some cases, the sintered material is formed by sintering one or more of powdered glass, powdered polymer, or powdered metal. In other cases, the sintered material is formed by sintering one or more of glass, metal, or polymer fibers. In still other cases, the sintered material is formed from the sintering of one or more of glass, polymer, or metal beads.

Porous substrates can also contain, but are not limited to, one or more non-cellulosic polymers, e.g. a synthetic polymer, a natural polymer, or a semisynthetic polymer. For example, the substrate can contain a polyester, such as polyglycolide, polylactic acid, polycaprolactone, polyethylene adipate, polyhydroxylalkanoate, polyhydroxybutyrate, poly(3-hydroxybutyrate-co-3-hydroxyvalerate, polyethylene terephthalate, polybutylene terephthalate, polytrimethylene terephthalate, polyethylene naphthalate, Vectran®. In some cases, the polymer is spunbound, such as a spunbound polyester.

Additional synthetic polymers include, but are not limited to nylon, polypropylene, polyethylene, polystyrene, divinylbenzene, polyvinyl, polyvinyl difluoride, high density polyvinyl difluoride, polyacrylamide, a ($C_2$-$C_6$) monoolefin polymer, a vinylaromatic polymer, a vinylaminoaromatic polymer, a vinylhalide polymer, a ($C_1$-$C_6$) alkyl (meth) acrylate polymer, a(meth)acrylamide polymer, a vinyl pyrrolidone polymer, a vinyl pyridine polymer, a ($C_1$-$C_6$) hydroxyalkyl (meth)acrylate polymer, a (meth)acrylic acid polymer, an acrylamidomethylpropylsulfonic acid polymer, an N-hydroxy-containing ($C_1$-$C_6$) alkyl(meth)acrylamide polymer, acrylonitrile or a mixture of any of the foregoing.

Porous substrates can also contain, but are not limited to, one or more polysaccharides. Exemplary polysaccharides include those containing cellulose, agarose, amylose, chitin, chitosan, galactosamine, curdlan, dextran, xylan, inulin, and derivatives thereof, e.g., esters, phenyl carbamates, alkyl carabmates, and benzyl carbamates. In some cases, the polysaccharides are cross-linked. For example, the porous substrate can include agarose, or a cross linked agarose. In some cases, the substrate can include cross links between the polysaccharide and other constituents of the substrate.

Porous substrates also include, but are not limited to, capillary wicking beds and materials used therein. For example, the substrate can include a thin layer chromatography plate, or be formed of any of the thin layer chromatography substrates known in the art. Thin layer chromatography substrates known in the art include, but are not limited to, silica, silica derivatized with $C_4$, $C_8$, or $C_{18}$ alkyl groups, and alumina. Porous substrates can also contain, but are not limited to, glass, glass fibers, fiberglass, natural or synthetic sponge, silica, alumina, or a derivative thereof. In some cases, the glass fiber is a glass fiber derivative. In some cases, the porous substrate contains glass fiber and another porous material such as cellulose, a cellulose derivative, and/or polyester.

In addition to the foregoing substrate materials, the substrate can also contain any combination of the foregoing. In some cases, the substrate can contain composite materials that include a combination of materials described above. For example, the substrate can contain glass or silica fibers in a synthetic polymer matrix. As another example, the porous substrate can contain plastic backed glass fiber, or plastic backed nitrocellulose. Additional suitable materials that may comprise the porous substrate include any of the materials, or a combination thereof, described in Jallerat & Thom, *Filter Membranes and Bioseparation Equipment and Supplies*, IVD Technology (October, 2004), or any of the materials described in U.S. Pat. No. 4,632,901; or U.S. Patent Application Nos. 2010/0239459, and 2013/0164193. In some embodiments, one or more regions of the porous substrate, or a portion thereof, is substantially compressible. As used herein, substantially compressible refers to a material that retains structural integrity under an applied pressure that compresses the material. For example, a porous substrate that is substantially compressible can be compressed along at least one axis such that the length of the compressed axis is reduced by at least about 1%, 2%, 3%, 4%, 5%, 6%, 7%, 8%, 9%, 10%, 15%, 20%, 25%, 30%, 33%, 40%, 50%, 60%, 66%, 75%, 80%, 90%, or more, without loss of structural integrity.

In some embodiments, the porous substrate is configured to enable detection of one or more analyte(s) by lateral flow in a lateral flow device (e.g., a sequential lateral flow device). For example, the porous substrate can be useful for contacting one or more binding reagents to one or more membrane-bound analytes by lateral flow in a sequential lateral flow device. In some cases, the sequential lateral flow device is a passive sequential lateral flow device. Exemplary passive sequential lateral flow devices are described in U.S. Patent Application Nos. 2010/0239459, and 2013/0164193.

The porous substrate can be suitable for storage. For example, the porous substrate can be stored for at least about a day, three days, 7-10 days, at least about a month, two months, 3 months, six months, a year or longer. In some cases, the porous substrate can be stored (e.g., at about 4, 5, 6, 7, 8, 10, 12, 14, 16, 18, 20, 22, 25, 30, 35, or 37° C. or more) for at least about a day, three days, 7-10 days, at least about a month, two months, 3 months, six months, a year or longer. The porous substrate can be stored dry, substantially dry, or wet. In some cases, a portion of the porous substrate is stored dry or substantially dry and a portion is stored wet. In some cases, a portion of the porous substrate is stored dry and a portion is stored substantially dry. The porous substrate can be stored and then removed from storage, optionally reconstituted, and then provided as described herein to detect one or more membrane-bound analytes.

The porous substrates can be suitable for storage of binding reagents. For example, one or more binding reagents can be contacted with a porous substrate (e.g., contacted with a reagent reservoir region or subregion of a porous substrate) and the porous substrate then stored (e.g., stored for at least about a day, three days, 7-10 days, at least about a month, two months, 3 months, six months, a year or longer). The stored porous substrate and one or more binding reagents can then be used to detect one or more analytes bound to a membrane. In some cases, the binding reagent is dried, or substantially dried, onto the porous substrate prior to storage. Dry or substantially dry binding reagents can be reconstituted during or prior to use in detecting membrane bound analytes by contact with an aqueous solution.

i. Reagent Reservoir Region and Lateral Flow Region

The porous substrate can have a reagent reservoir region and a lateral flow region. In some embodiments, the reagent reservoir region is a reservoir for one or more binding reagents (e.g., one or more primary and/or one or more secondary antibodies). In some embodiments, the lateral flow region is a region of the porous substrate configured to wick one or more binding reagents, or a portion thereof, from the reagent reservoir region and through the lateral flow region, or a portion thereof. The reagent reservoir region of the porous substrate can be separated from the lateral flow region of the porous substrate by a barrier such that the lateral flow region does not wick solution or reagents from the reagent reservoir region until lateral flow is initiated. Such barriers include hydrophobic or impermeable barriers that are further described herein.

In some embodiments, the reagent reservoir region contains a reversibly immobilized binding reagent, such as an antibody. In some cases, the reversibly immobilized binding reagent is present on or in the reagent reservoir region in a dry or substantially dry state. In other embodiments, the reversibly immobilized binding reagent is present on or in the reagent reservoir region in solution. In some cases, the reagent reservoir region is a sponge, adsorbant, or absorbant that reversibly contains, or can reversibly contain, a binding reagent (e.g., in solution, dry, or substantially dry). In some embodiments, the reagent reservoir region is configured to be contacted with a solution containing a binding reagent and thereby reversibly immobilize the binding reagent. In some embodiments, the reagent reservoir region is configured to be contacted with a solution containing a binding reagent and then dried or substantially dried, thereby reversibly immobilizing the binding reagent.

In some embodiments, the reagent reservoir region is composed of the same material as the lateral flow region. In other embodiments, the reagent reservoir region is composed of a different material as compared to the lateral flow region. For example, the reagent reservoir region and lateral flow region can have a different pore size, thickness, composition, etc. In some cases, the reagent reservoir region is the same or substantially the same width as the lateral flow region. In some cases, the reagent reservoir region is the same or substantially the same height (i.e., thickness) as the lateral flow region. In other embodiments, the reagent reservoir region is thicker than the lateral flow region, and therefore has a greater height (e.g., a greater height in a non-compressed state). For example, the reagent reservoir region can be at least about 1.1, 1.2, 1.3, 1.5, 1.7, 2.0, 2.2, 2.5, 3-fold or more thicker than the lateral flow region. In some embodiments, the reagent reservoir region is thinner than the lateral flow region.

In some embodiments, the reagent reservoir region has two or more (e.g., at least 2, 3, 4, 5, 6, 7, 8, 9, 10, 11, 12, 13, 14, 15, 16, 17, 18, 19, 20, or more) reagent reservoir sub-regions. In some cases, the two or more reagent reservoir sub-regions enable detection of multiple analytes. For example, one reagent reservoir sub-region can be used to reversibly immobilize a first primary binding reagent that detects a first analyte and a second reagent reservoir sub-region can be used to reversibly immobilize a second primary binding reagent that detects a second analyte, etc. In some cases, the number of reagent reservoir sub-regions determines the number of different analytes that can be detected in a single blotting experiment. For example, a different primary binding reagent that specifically binds to a different analyte can be contacted with, or present in, each reagent reservoir sub-region. Alternatively, if the analytes to be detected are expected to be irreversibly immobilized in different locations on a membrane, multiple primary binding reagents (e.g., 2, 3, 4, or more) can be used in a single reagent reservoir region or sub-region. Reagent reservoir sub-regions can be separated by hydrophobic or impermeable barriers so that a detection reagent in one sub-region does not migrate, wick, or otherwise flow from one reagent reservoir sub-region into another reagent reservoir sub-region.

In some embodiments, porous substrates containing at least two or more reagent reservoir sub-regions have a corresponding number of lateral flow sub-regions. In some cases, the corresponding lateral flow sub-regions are not in fluid communication until initiation of lateral flow. For example, the reagent reservoir and lateral flow sub regions can be separated from their corresponding sub-regions by a hydrophobic or impermeable barrier. Thus, upon initiation of lateral flow, the binding reagent, or a portion thereof, in each reagent reservoir sub-region flows through at least a portion of the corresponding lateral flow sub-region. Lateral flow sub-regions can be separated by hydrophobic or impermeable barriers so that a primary or secondary binding reagent in one sub-region does not migrate, wick, or otherwise flow from one lateral flow sub-region into another lateral flow sub-region.

Figure 1:
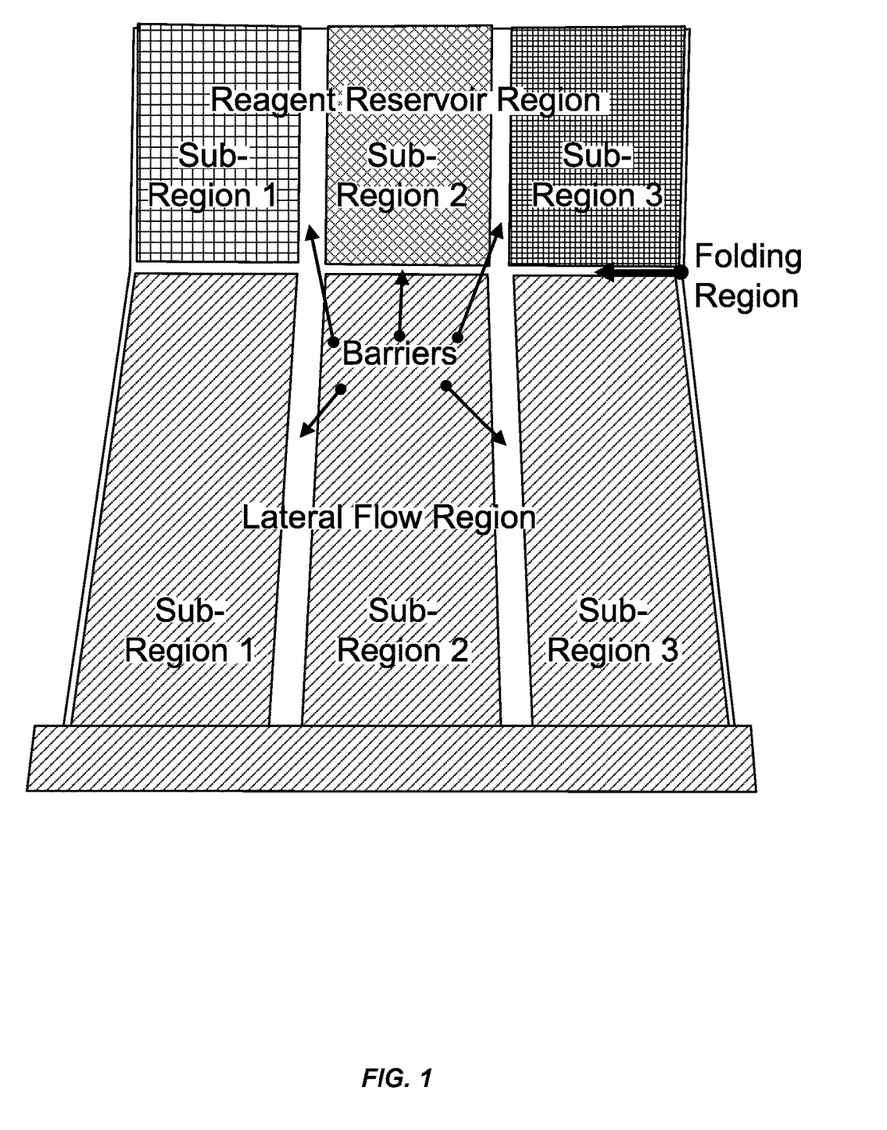
FIG. 1 depicts a porous substrate with three separate reagent reservoir sub-regions and three separate corresponding lateral flow sub-regions. The sub-regions are all separated by hydrophobic barriers so that there is no flow of binding reagents between sub-regions. The reagent reservoir sub-regions are loaded with different binding reagents to enable detection of multiple analytes.
Figure 2:
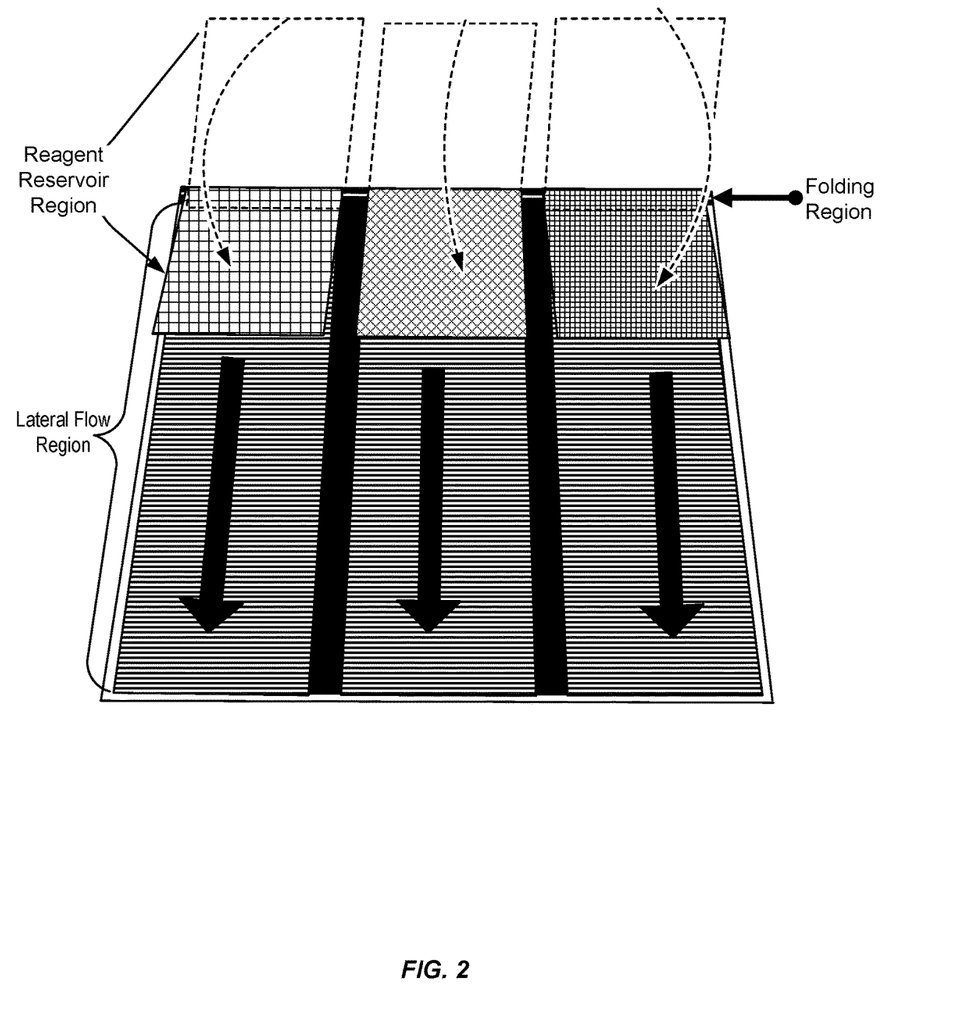
FIG. 2 depicts folding of the porous substrate at the folding region so that the reagent reservoir region contacts the lateral flow sub-region, thereby initiating lateral flow of reagents in the direction indicated by the arrows. The hydrophobic barriers block flow of reagents from between lateral flow sub-regions during lateral flow.

FIG. 1 is an exemplary embodiment of a porous substrate having a reagent reservoir region and a lateral flow region, each region separated into a number of sub-regions by hydrophobic barriers. In FIG. 1, the reagent reservoir region is loaded with three different binding reagents, each separated from each other by a hydrophobic barrier. The reagent reservoir regions are also each separated from their corresponding lateral flow sub-region by a hydrophobic barrier. As shown in FIG. 2, contacting the reagent reservoir region to the lateral flow region (e.g., by folding) initiates lateral flow. Thus, as depicted, at least three different membrane-bound analytes can be detected (e.g., in parallel) by the three different binding reagents. However, it will be appreciated that a number other than three (e.g., 2, 4, 5, 6, 7, 8, etc.) can be similarly run in parallel.

In some cases, the porous substrate contains a liquid sink. A liquid sink is a component of the porous substrate having a liquid absorbing capacity that is significantly larger than that of the lateral flow region. In some embodiments, the liquid sink is configured such that, upon initiation of lateral flow, liquid flows from the reagent reservoir region to the lateral flow region and into the liquid sink. In some cases, the liquid sink is an integral component of the porous substrate. In some cases, the liquid sink is a distinct component of the porous substrate. In some cases, the liquid sink is configured or comprised of material that facilitates the rate of lateral flow through the lateral flow region. In some embodiments, the liquid sink is comprised of the same material as the lateral flow region. In some embodiments, the liquid sink is comprised of different materials as compared to the lateral flow region. The liquid sink can be comprised of any of the porous substrate materials described herein, or a combination thereof. In some cases, the liquid sink is thicker (e.g., at least about 1.1, 1.2, 1.3, 1.5, 1.7, 2.0, 2.2, 2.5, 3-fold or more thicker than the lateral flow region).

ii. Folding Region

In some embodiments, the porous substrate contains a folding region. In general, the folding region is situated and configured to allow contacting the reagent reservoir region, or a portion thereof, with the lateral flow region, or a portion thereof, thereby initiating lateral flow. The folding region can extend the width of the porous substrate or a portion thereof. In some cases, the folding region lies within, or adjacent to the reagent reservoir region. In some cases, the folding region lies within, or adjacent to the lateral flow region. In some cases, the folding region lies between the reagent reservoir region and the lateral flow region. In some cases, the folding region lies within or adjacent to an impermeable or hydrophobic barrier between the reagent reservoir region and the lateral flow region. In some cases, the folding region is demarcated. In some cases, the demarcation is a visual line or other mark identifying the location or approximate location of the folding region. In some cases, the demarcation is a crease or pleat of the porous substrate.

iii. Barriers

The porous substrate can contain one or more barriers, such as one or more hydrophobic barriers or one or more impermeable barriers. In some cases, the porous substrate has one or more barriers between a reagent reservoir region and a lateral flow region. In some cases, the porous substrate has one or more barriers between a reagent reservoir sub-region and another reagent reservoir sub-region. In some cases, the porous substrate has one or more barriers between a lateral flow sub-region and another lateral flow sub-region. In some cases, the porous substrate has one or more barriers between one or more reagent reservoir sub-regions and one or more lateral flow sub-regions. In some embodiments, one or more porous substrate barriers inhibit, eliminate, or substantially eliminate fluid communication (e.g., flow) between adjacent regions or sub-regions. In some cases, one or more porous substrate barriers inhibit, eliminate, or substantially eliminate fluid communication (e.g., flow) between adjacent regions or sub-regions until lateral flow is initiated.

Suitable barriers include hydrophobic barriers such as wax barriers, or barriers created by vapor or liquid phase silanization of the porous substrate. Suitable barriers also include impermeable barriers, such as barriers comprising a plastic, polymer, or resin. In some cases, the impermeable barriers are frames that support a hydrophilic transfer sheet suspended within the frame. In some cases, the barriers are comprised of a combination of hydrophobic (e.g., wax or silanized cellulose) and impermeable barriers. For example, in some cases, the porous substrates are surrounded by impermeable (e.g., plastic or resin) barrier frames and are further subdivided by wax or silanized cellulose barriers.

The wax used to form the wax barriers can be any wax that is flowable at elevated temperatures and non-flowable at ambient temperature (e.g., about 20-25° C.). Examples are paraffin waxes, microcrystalline waxes, thermoset waxes, animal waxes such as beeswax, lanolin, and tallow, vegetable waxes such as soy, carnauba, candelilla and palm waxes, mineral waxes such as ceresin and montan waxes, petroleum waxes, and synthetic waxes such as ethylenic polymers, chlorinated naphthalenes, and Fischer-Tropsch waxes. Paraffin wax compositions may contain, in addition to n-paraffins and isoparaffins, minor amounts of cycloparaffins or olefins, or both. Waxes that become flowable, i.e., that have melting points, within the temperature range of from about 60° C. to about 150° C., or from about 75° C. to about 125° C., are among those that can be used. Wax formulations and compositions that behave in this manner are known to those of skill in the art.

The silanization reagent used to form hydrophobic barriers can be any silanization reagent that reacts with the porous substrate, or a portion thereof. For example, if the porous substrate contains cellulose, a silanization reagent that silanizes hydroxyl groups of the cellulose backbone can be utilized. Exemplary silanization reagents include, but are not limited to, trimethylchlorosilane, trimethylsilane, or hexamethyldisilazane. Silanization reagents further include triethoxysilanes ($R-Si(C_2H_5O)_3$) where R is, for example, vinyl, methacrylol, aminopropyl, fluoroalkyl, or thioethyl. Other suitable silanization reagents will be readily apparent to those of skill in the art.

The wax or other barrier forming reagent (e.g., silanization reagent, or impermeable barrier) can be applied to one side or both sides of the porous substrate, although in most cases, application to one side will be sufficient provided that the porous substrate penetrates, or is made to penetrate (e.g., by melting after application), the porous substrate to a degree sufficient to serve as a barrier to the flow of liquid. The barrier forming reagent can be applied as a liquid. The liquid can be applied by hand or other apparatus. In some cases, the liquid is sprayed or poured onto the porous substrate. Spraying can be accomplished with an inkjet printer or similar apparatus. In some cases, the liquid hardens after application to form an impermeable and/or hydrophobic barrier. Alternatively, the barrier forming reagent can be applied as a vapor. For example, a silanization reagent, wax, plastic, resin, or polymer can be applied as a vapor that condenses on the porous substrate or reacts with the porous substrate. Alternatively, the barrier forming reagent can be applied as a solid. For example, wax can be applied as a solid manually or in an automated or mechanized fashion. In some cases, the porous substrate is masked to protect regions from the barrier forming reagent, and the barrier forming reagent is contacted with the porous substrate.

Application of wax can be achieved by hand, either by the use of a common crayon or by a wax pen, or by a wax printer. Wax pens are known in the art and commonly include a housing having a reservoir to contain hot wax, a spout, and a handle. Application of the hot wax is achieved by tipping the housing to cause the liquefied wax to pass through the spout, and the housing is equipped with a valve to stop the flow of the wax at the terminus of a printed line. Wax printers are likewise known in the art and commonly operated by thermal transfer printing using a print head that includes an array of very small heating elements that are software-controlled for independent activation to produce localized heating of the wax above its melting point to release the wax to the print medium. Commercially available examples of wax printers include the Phaser 8560DN (Fuji Xerox, Ltd., Japan), and the CALCOMP COLORMASTER PLUS thermal wax transfer printer (CalComp Graphics, LLC, Foothill Ranch, Calif., USA). Descriptions of wax printers and their use can be found in Kroon (Tektronix, Inc.), U.S. Pat. No. 5,957,593 (Sep. 28, 1999); Lin (Xerox Corporation), U.S. Pat. No. 8,206,664 (Jun. 26, 2012); Lu, Y., et al., "Rapid prototyping of paper-based microfluidics with wax for low-cost, portable bioassay,"

*Electrophoresis* 2009, 30, 1497-1500; and Carrilho, E., et al., "Understanding Wax Printing: A Simple Micropatterning Process for Paper-Based Microfluidics," *Anal. Chem.*, 2009, 81 (16), 7091-7095. The width of a wax line as applied (prior to heating) can vary and is not critical to the present invention, provided that the amount of wax contained within the line is sufficient to penetrate the porous substrate and form a barrier to the lateral flow of fluid within the porous substrate.

In some embodiments, once applied, the wax can be made to penetrate the bulk thickness of the porous substrate to fill the pores and form a lateral barrier to aqueous fluid flow by heating the wax above its melting point. In some cases, the amount of wax applied will be such that full penetration of the thickness of the sheet with the melted wax will occur while lateral flow of the melted wax (i.e., in directions parallel to the flat faces of the sheet) is minimal or at least limited to a small distance that is substantially uniform along the length of a line of applied wax so that the resulting area bordered by the wax barrier is known and controlled. The formation of the barrier in this manner can also be controlled by the degree of heating, including the temperature to which the wax is heated and the length of time that the heating is continued. Optimal temperatures and durations are readily determinable by routine trial and error, but in most cases serviceable results will be obtained by heating to at least 5° C. above the wax melting point, and in many cases from about 5 to about 50° C. above the melting point, or from about 10 to about 30° C. above the melting point. The most appropriate heating time will depend on the temperature, higher temperatures requiring less time. In general, heating times ranging from about fifteen seconds to about twenty minutes, or in many cases from about thirty seconds to about ten minutes, will provide useful results. Heating can be achieved by conventional means, including radiative heating, conductive heating, convective heating, impulse heating, and microwave heating. Effective results can be achieved with equipment as simple as a hot plate or a conventional oven.

Optimal widths for hydrophobic or impermeable barriers may vary with the dimensions of the area to be bordered by the barrier and with the thickness of the porous substrate and are readily determinable by routine testing. In most cases, the width will range from about 10 microns to about 5 mm, from about thirty microns to about 3 mm, from about 100 microns to about 1 mm, or from about 200 microns to about 5 mm, or 10 mm.

B. Detection Reagents i. Binding Reagents

Binding reagents are described herein for detection of analytes. In some cases, the binding reagents are antibodies (e.g., primary or secondary antibodies). Primary antibodies can be used to bind to an analyte. In some cases, the primary antibody is labeled enabling detection of the primary antibody and consequently detection of the analyte. In some cases, the primary antibody is detected by binding to a labeled secondary binding reagent, such as a labeled secondary antibody. In some cases, tertiary binding reagents are utilized to detect complexes containing the analyte and the primary and secondary binding reagent.

In some embodiments, the porous substrate contains multiple (e.g., 2, 3, 4, 5, 6, 7, 8, 9, 10, 11, 12, 13, 14, 15, or more) reagent reservoir sub-regions, and a corresponding number of binding reagents (e.g., primary binding reagents such as primary antibodies). In some cases, the porous substrate contains multiple primary binding reagents and primary binding reagents are different in that they each detect a different analyte. In some cases, one or more of the primary binding reagents are the same in that they detect the same analyte. In some cases, the porous substrate contains 1, 2, 3, 4, 5, 6, 7, 8, 9, 10, 11, 12, 13, or 14 fewer binding reagents than reagent reservoir sub-regions. In some cases, a porous substrate containing multiple reagent reservoir sub-regions is provided to a customer or end-user and one or more binding reagents are contacted to the reagent reservoir by the customer or end-user.

Binding reagents can be provided on or in the porous substrate or can be supplied separately. In some cases, a porous substrate contains one or more binding reagents dried thereon. The dried binding reagent(s) can be reconstituted by contacting the reagent reservoir region with an aqueous solution. In some cases, the aqueous reconstitution buffer can contain one or more re-wetting reagents including salts, buffers, or a protein aggregation modifying agent as described herein. Alternatively, the binding reagent can be present in the porous substrate in a solution. In some cases, the binding reagent(s) are stored in the porous substrate (e.g., the reagent reservoir region). For example, binding reagent(s) can be stored dry, substantially dry, or in solution in the porous substrate for at least about a day, three days, 7-10 days, at least about a month, two months, 3 months, six months, a year or longer. In some cases, the binding reagents and porous substrate are suitable for storage (e.g., at about 4, 5, 6, 7, 8, 10, 12, 14, 16, 18, 20, 22, 25, 30, 35, or 37° C. or more) for at least about a day, three days, 7-10 days, at least about a month, two months, 3 months, six months, a year or longer.

ii. Labels

Analytes can be detected by detecting a label that is linked to a binding reagent. The label can be linked directly to the binding reagent (e.g., by a covalent bond) or the attachment can be indirect (e.g., using a chelator or linker molecule). The terms "label" and "detectable label" are used synonymously herein. In some embodiments, each label (e.g., a first label linked to a first binding reagent, a second label linked to a second binding reagent, etc.) generates a detectable signal and the signals (e.g., a first signal generated by the first label, a second signal generated by the second label, etc.) are distinguishable. In some embodiments, the two or more binding reagent labels comprise the same type of agent (e.g., a first label that is a first fluorescent agent and a second label that is a second fluorescent agent). In some embodiments, the two or more binding reagent labels (e.g., the first label, second label, etc.) combine to produce a detectable signal that is not generated in the absence of one or more of the labels.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, colloidal gold, and combinations thereof. In some embodiments, the label can include an optical agent such as a chromophore, fluorescent agent, phosphorescent agent, chemiluminescent agent, etc. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Chromophores include co-enzymes or co-factors that have a detectable absorbance. In some cases, a binding reagent can be detected by detecting the intrinsic absorbance of a peptide bond at, e.g., 220 or 280 nm.

Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye. In some embodiments, a fluorescent agent is a polymer dot or a quantum dot. Fluorescent dyes and fluorescent label reagents include those which are commercially available, e.g., from Invitrogen/Molecular Probes (Eugene, Oreg.) and Pierce Biotechnology, Inc. (Rockford, Ill.). In some embodiments, the optical agent is an intercalating dye. In some embodiments, 2, 3, 4, 5, or more binding reagents are each labeled with an optical agent such as a fluorescent agent (e.g., a first binding reagent labeled with a first fluorescent label, a second binding reagent labeled with a second fluorescent label, etc.), and each binding reagent that is labeled with an optical agent is detected by detecting a signal generated by the optical agent (e.g., a fluorescent signal generated by a fluorescent label). In some embodiments, all of the binding reagents are labeled with an optical agent, and each optical agent-labeled binding reagent is detected by detecting a signal generated by the optical agent.

In some embodiments, the label is a radioisotope. Radioisotopes include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In some embodiments, 2, 3, 4, 5, or more binding reagents are each labeled with a radioisotope (e.g., a first binding reagent labeled with a first radioisotope, a second binding reagent labeled with a second radioisotope, etc.), and each binding reagent that is labeled with a radioisotope is detected by detecting radioactivity generated by the radioisotope. For example, one binding reagent can be labeled with a gamma emitter and one binding reagent can be labeled with a beta emitter. Alternatively, the binding reagents can be labeled with radionuclides that emit the same particle (e.g., alpha, beta, or gamma) at different energies, where the different energies are distinguishable. In some embodiments, all of the binding reagents are labeled with a radioisotope and each labeled binding reagent can be detected by detecting radioactivity generated by the radioisotope.

In some embodiments, the label is an enzyme, and the binding reagent is detected by detecting a product generated by the enzyme. Examples of suitable enzymes include, but are not limited to, urease, alkaline phosphatase, (horseradish) hydrogen peroxidase (HRP), glucose oxidase, β-galactosidase, luciferase, alkaline phosphatase, and an esterase that hydrolyzes fluorescein diacetate. For example, a horseradish-peroxidase detection system can be used with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, which yields a soluble product readily detectable at 405 nm. A β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.). In some embodiments, 2, 3, 4, 5, or more binding reagents are each labeled with an enzyme (e.g., a first binding reagent labeled with a first enzyme, a second binding reagent labeled with a second enzyme, etc.), and each binding reagent that is labeled with an enzyme is detected by detecting a product generated by the enzyme. In some embodiments, all of the binding reagents are labeled with an enzyme, and each enzyme-labeled binding reagent is detected by detecting a product generated by the enzyme.

In some embodiments, the label is an affinity tag. Examples of suitable affinity tags include, but are not limited to, biotin, peptide tags (e.g., FLAG-tag, HA-tag, His-tag, Myc-tag, S-tag, SBP-tag, Strep-tag, eXact-tag), and protein tags (e.g., GST-tag, MBP-tag, GFP-tag).

In some embodiments, the label is a nucleic acid label. Examples of suitable nucleic acid labels include, but are not limited to, oligonucleotide sequences, single-stranded DNA, double-stranded DNA, RNA (e.g., mRNA or miRNA), or DNA-RNA hybrids. In some embodiments, the nucleic acid label is about 10, 15, 20, 25, 30, 35, 40, 45, 50, 60, 70, 80, 90, 100, 150, 200, 250, 300, 350, 400, 450, 500, 600, 700, 800, 900, or 1000 nucleotides in length.

In some embodiments, the label is a nucleic acid barcode. As used herein a "barcode" is a short nucleotide sequence (e.g., at least about 4, 6, 8, 10, or 12, nucleotides long) that uniquely defines a labeled molecule, or a second molecule bound to the labeled binding reagent. The length of the barcode sequence determines how many unique samples can be differentiated. For example, a 4 nucleotide barcode can differentiate $4^4$ or 256 samples or less, a 6 nucleotide barcode can differentiate 4096 different samples or less, and an 8 nucleotide barcode can index 65,536 different samples or less. The use of barcode technology is well known in the art, see for example Katsuyuki Shiroguchi, et al. Digital RNA sequencing minimizes sequence-dependent bias and amplification noise with optimized single-molecule barcodes, PNAS (2012); and Smith, A M et al. Highly-multiplexed barcode sequencing: an efficient method for parallel analysis of pooled samples, Nucleic Acids Research Can 11, (2010).

In some embodiments, the label is a "click" chemistry moiety. Click chemistry uses simple, robust reactions, such as the copper-catalyzed cycloaddition of azides and alkynes, to create intermolecular linkages. For a review of click chemistry, see Kolb et al., *Agnew Chem* 40:2004-2021 (2001). In some embodiments, a click chemistry moiety (e.g., an azide or alkyne moiety) can be detected using another detectable label (e.g., a fluorescently labeled, biotinylated, or radiolabeled alkyne or azide moiety).

Techniques for attaching detectable labels to binding reagents such as proteins (e.g., antibodies) are well known. For example, a review of common protein labeling techniques can be found in *Biochemical Techniques: Theory and Practice*, John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996).

In some embodiments, two or more labels (e.g., a first label, second label, etc.) combine to produce a detectable signal that is not generated in the absence of one or more of the labels. For example, in some embodiments, each of the labels is an enzyme, and the activities of the enzymes combine to generate a detectable signal that is indicative of the presence of the labels (and thus, is indicative of each of the labeled proteins). Examples of enzymes combining to generate a detectable signal include coupled assays, such as a coupled assay using hexokinase and glucose-6-phosphate dehydrogenase; and a chemiluminescent assay for NAD (P)H coupled to a glucose-6-phosphate dehydrogenase, beta-D-galactosidase, or alkaline phosphatase assay. See, e.g., Maeda et al., *J Biolumin Chemilumin* 1989, 4:140-148.

C. Protein Aggregation Modifying Agents

Described herein are protein aggregation modifying agents. Protein aggregation modifying agents can be utilized to reduce or eliminate aggregation or denaturation of binding reagents, such as proteins (e.g., antibodies), stored on, or delivered from, a porous substrate. For example, protein aggregation modifying agents can be utilized to reduce or eliminate aggregation or denaturation of primary antibodies stored in, or delivered from, the reagent reservoir region of a porous substrate. In some cases, protein aggregation modifying agents can be utilized to facilitate lateral flow of binding reagents in the lateral flow region of the porous substrate.

In some cases, protein aggregation modifying agents that act to displace proteins from the air-water interface and thereby protect them from denaturation and aggregation are particularly effective in reducing the aggregation of binding reagents immobilized on a porous substrate. In other cases, the protein aggregation modifying agent directly affects the stability of the binding reagent by binding to the binding reagent and/or stabilizing the binding reagent. In other cases, the protein aggregation modifying agent acts to shift the equilibrium away from a denatured or unfolded state and thus reduce aggregation. For example, in some cases, the interaction between the protein aggregation modifying agent and the binding reagent is thermodynamically disfavored due to strong repulsion between an amide backbone of the binding reagent and the protein aggregation modifying agent. Thus, unfolding of the binding reagent in the presence of the protein aggregation modifying agent is disfavored because unfolding exposes more amide backbone surface to the protein aggregation modifying agent.

Protein aggregation modifying agents can be one or more of a cyclodextrin, a non-ionic surfactant, an ionic surfactant, a zwitterionic surfactant, a non-detergent sulfobetaine, a simple sugar, a polysaccharide, a polyol, an organic solvent, an aggregation modifying protein, a disordered peptide sequence, an amino acid, an oxido-reduction agent, a lyoprotectant, a cryoprotectant, or a chaotropic agent.

Cyclodextrins can be, but are not limited to, α-cyclodextrin, β-cyclodextrin, γ-cyclodextrin, (2,3,6-tri-O-methyl)-β-cyclodextrin, (2,3,6-tri-O-methyl)-β-cyclodextrin, (2-hydroxy)propyl-β-cyclodextrin, (2-hydroxy)propyl-γ-cyclodextrin, random methyl-β-cyclodextrin, random methyl-γ-cyclodextrin, carboxymethyl-β-cyclodextrin, carboxymethyl-γ-cyclodextrin, 6-monodeoxy-6-monoamino-β-cyclodextrin, sulfobutyl-β-cyclodextrin, 6-amino-6-deoxy-β-cyclodextrin, acetyl β-cyclodextrin, succinyl α-cyclodextrin, succinyl β-cyclodextrin, succinyl γ-cyclodextrin, (2,3,6-tri-O-benzoyl)-β-cyclodextrin, succinyl-(2-hydroxypropyl)-β-cyclodextrin, or succinyl-(2-hydroxypropyl)-γ-cyclodextrin. Cyclodextrins can also be a cyclodextrin polymer containing one or more of the foregoing cyclodextrin molecules. Additional cyclodextrins are known in the art, and include, e.g. those described on the world wide web at cyclodextrin.com. Exemplary concentrations of cyclodextrins are, without limitation, about 1 mM, 2 mM, 2.5 mM, 5 mM, 7.5 mM, 10 mM, 15 mM, 20 mM, 25 mM, 50 mM, 75 mM, or 100 mM.

Non-ionic surfactants can be polyethylene-sorbitan-fatty acid esters, polyethylene-polypropylene glycols or polyoxyethylene-stearates. Polyethylene-sorbitan-fatty acid esters can be polyethylene(20)-sorbitan-esters (Tween 20™) or polyoxyethylene(20)-sorbitanmonooleate (Tween 80™). Polyethylene-polypropylene glycols can be polyoxypropylene-polyoxyethylene block co-polymers such as those sold under the names Pluronic® or Poloxamer™ Polyoxyethylene-stearates can be, for example, those sold under the trademark Myrj™ Exemplary, polyoxyethylene monolauryl ethers include those sold under the trademark Brij™, e.g., Brij-35. Exemplary concentrations of non-ionic surfactants are, without limitation, about 0.01%, 0.02%, 0.05%, 0.1%, 0.2%, 0.5%, 0.75%, 1%, 2%, 2.5%, 5%, 7.5%, or about 10% w/w, w/v, or v/v.

Ionic surfactants can be anionic surfactants or cationic surfactants. Anionic surfactants useful in the present invention can be, but are not limited to, soaps including alkali soaps, such as sodium, potassium or ammonium salts of aliphatic carboxylic acids, usually fatty acids, such as sodium stearate. Additional anionic surfactants include organic amine soaps such as organic amine salts of aliphatic carboxylic acids, usually fatty acids, such as triethanolamine stearate. Cationic surfactants useful in the present invention include, but are not limited to, amine salts such as octadecyl ammonium chloride or quarternary ammonium compounds such as benzalkonium chloride. Ionic surfactants can include the sodium, potassium or ammonium salts of alkyl sulfates, such as sodium dodecyl sulfate or sodium octyl sulfate. Exemplary concentrations of ionic surfactants are, without limitation, about 0.01%, 0.02%, 0.05%, 0.1%, 0.2%, 0.5%, 0.75%, 1%, 2%, 2.5%, 5%, 7.5%, or about 10% w/w, w/v, or v/v.

Zwitterionic surfactants have both cationic and anionic centers attached to the same molecule. The cationic part is, e.g., based on primary, secondary, or tertiary amines or quaternary ammonium cations. The anionic part can be a sulfonate, as in CHAPS (3-[(3-Cholamidopropyl)dimethylammonio]-1-propanesulfonate). Other anionic groups are sultaines illustrated by cocamidopropyl hydroxysultaine or betaines, e.g., cocamidoethyl betaine, cocamidopropyl betaine, or lauramidopropyl betaine. Exemplary concentrations of zwitterionic surfactants are, without limitation, about 0.01%, 0.02%, 0.05%, 0.1%, 0.2%, 0.5%, 0.75%, 1%, 2%, 2.5%, 5%, 7.5%, and about 10% w/w, w/v, or v/v.

Non detergent sulfobetaines (NDSBs) have a sulfobetaine hydrophilic group and a short hydrophobic group that cannot aggregate to form micelles, therefore NDSBs are not considered detergents. Exemplary NDSBs include, but are not limited to NDSB 256, NDSB 221, NDSB 211, NDSB 201, NDSB 195, 3-(4-tert-Butyl-1-pyridinio)-1-propanesulfonate, 3-(1-pyridinio)-1-propanesulfonate, 3-(Benzyldimethylammonio) propanesulfonate, or Dimethylethylammoniumpropane sulfonate. Exemplary concentrations of NDSBs include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Polyols are compounds with multiple hydroxyl functional groups. In some cases, polyols can modify the aggregation or denaturation behavior of a protein by a variety of mechanisms. For example, in some cases, the polyol can shift the equilibrium to the folded state by presenting a thermodynamically disfavored interaction with the protein backbone. Alternatively, in some cases, the polyol can bind to and stabilize the folded state of the protein.

Polyols can be simple sugars such as sucrose, mannitol, sorbitol, inositol, xylitol, erythritol, glucose, galactose, raffinose, or trehalose. Polyols can also be polysaccharides such as dextran, starch, hydroxyethyl starch, or polymers containing one or more of the simple sugars described herein. Glycerol, ethylene glycol, polyethylene glycol, pentaerythritol propoxylate, and pentaerythritol propoxylate, and combinations thereof are also exemplary polyols.

Organic solvents can be, but are not limited to, those organic solvent that are known to inhibit denaturation, unfolding, or aggregation of one or more proteins. A variety of suitable organic solvents are known in the art. For example, organic solvents can include ethanol, butanol, propanol, phenol, dimethyl formamide, 2-methyl-2,4-pentanediol, 2,3-butanediol, 1,2-propanediol, 1,6-hexanediol, or dimethyl sulfoxide.

Aggregation modifying proteins can be proteins known in the art to inhibit denaturation, unfolding, or aggregation of one or more proteins. Exemplary aggregation modifying proteins include, but are not limited to, albumins. Albumins are proteins that are water-soluble, are moderately soluble in concentrated salt solutions, and experience heat denaturation. Exemplary albumins include serum albumins (e.g., bovine, horse, or human serum albumin) or egg albumin (e.g., hen egg-white albumin). Other exemplary aggregation modifying proteins include casein, gelatin, ubiquitin, lysozyme, or late embryogenesis abundant (LEA) proteins. LEA proteins include LEA I, LEA II, LEA III, LEA IV, LEA V, or atypical LEA proteins. LEA proteins are known in the art and described, e.g., in Goyal K., et al., Biochemical Journal 288(pt. 1), 151-57, (2005).

Protein aggregation modifying agents can also be amino acids. In some cases, the amino acids can serve an oxido-reduction function to maintain an appropriate oxidative potential for the protein immobilized on the substrate. Suitable oxido-reductive amino acids include cysteine and cystine. Other amino acids serve to reduce denaturation or aggregation through a non-oxido-reductive method. For example, arginine, glycine, proline, and taurine have been shown to reduce protein aggregation.

Other oxido-reduction agents can be employed to reduce protein aggregation. Oxido-reductants other than cysteine and cystine, can be used to optimize the reduction potential in the substrate onto which the protein is immobilized. Exemplary oxido-reductants include mercaptoethanol, dithiothreitol, dithioerythritol, tris(2-carboxyethyl)phosphine, glutathione, glutathione disulfide, and oxidized derivatives thereof, as well as $Cu^{2+}$.

Protein aggregation modifying agents can also include lyoprotectants, cryoprotectants, or chaotropic agents. In some cases, the protein aggregation modifying agent is a chaotrope such as urea, thiourea, guanidinium, cyanate, thiocyanate, trimethylammonium, tetramethylammonium, cesium, rubidium, nitrate, acetate, iodide, bromide, trichloroacetate, or perchlorate. Under certain conditions, such as at low concentrations, chaotropes can reduce protein aggregation. Other protein aggregation modifying agents include trimethylamine N-oxide.

Protein aggregation modifying agents can be salts. Exemplary salts include, but not limited to, the sodium, potassium, magnesium, or calcium salts of chloride, sulfate, or phosphate. Protein aggregation modifying agents can also be buffering agents. Exemplary buffering agents include, but are not limited to, tris(hydroxymethyl) amino methene (TRIS), TAPSO, MES, HEPES, PIPES, CAPS, CAPSO, MOPS, MOPSO, or sodium or potassium phosphate, carbonate, bicarbonate, citrate, acetate, or borate buffers.

The protein aggregation modifying agents can be provided in any suitable concentration. In some cases, the protein is provided as an aqueous solution containing binding reagent and protein aggregation modifying agents. In such cases, the solution can be contacted with a porous substrate and, optionally, dried. Exemplary concentrations of protein aggregation modifying agents in the aqueous binding reagent solution include, but are not limited to, about 0.001%, 0.005%, 0.01%, 0.05%, 0.1%, 0.5%, 1%, 2%, 4%, 5%, 10%, 20%, or about 25% or more w/v of the solution. Further exemplary concentrations include, but are not limited to, about 1 μM, 5 μM, 10 μM, 25 μM, 50 μM, 75 μM, 100 μM, 150 μM, 200 μM, 300 μM, 500 μM, 750 μM, 1 mM, 5 mM, 10 mM, 25 mM, 50 mM, 100 mM, 150 mM, 200 mM, 300 mM, 500 mM, and 1M.

In some cases, the protein aggregation modifying agents are provided on the porous substrate. Exemplary compositions containing a protein aggregation modifying agent and a porous substrate include, substrates, or regions therein (e.g., a reagent reservoir region) that contain about 0.001%, 0.005%, 0.01%, 0.05%, 0.1%, 0.5%, 1%, 2%, 3%, 4%, 5%, or about 10%, 20%, or about 25% by weight of one or more protein aggregation modifying agents.

Protein aggregation modifying agents can be provided in any suitable combination. For example, in some cases, 1, 2, 3, 4, 5, 6, 7, 8, 9, 10 or more of the foregoing protein aggregation modifying agents can be utilized to reduce aggregation of a binding reagent reversibly immobilized on a porous substrate. In some cases, prior to contacting the porous substrate with the binding reagent solution, the porous substrate contains a protein aggregation modifying agent, and the binding reagent solution contains the same, or a different, protein aggregation modifying agent. In some cases, prior to contacting the substrate with the binding reagent solution, the substrate contains a protein aggregation modifying agent, and the binding reagent solution does not contain a protein aggregation modifying agent. In some cases, prior to contacting the substrate with the binding reagent solution, the binding reagent solution contains a protein aggregation modifying agent and the substrate, or the region to be contacted, does not.

IV. Methods

Compositions and methods described herein can be utilized to detect one or more analytes. For example, compositions and methods can be utilized to detect one or more analytes that are irreversibly bound to a membrane. In some cases, compositions and methods described herein can be utilized to perform a blotting experiment.

Figure 3:
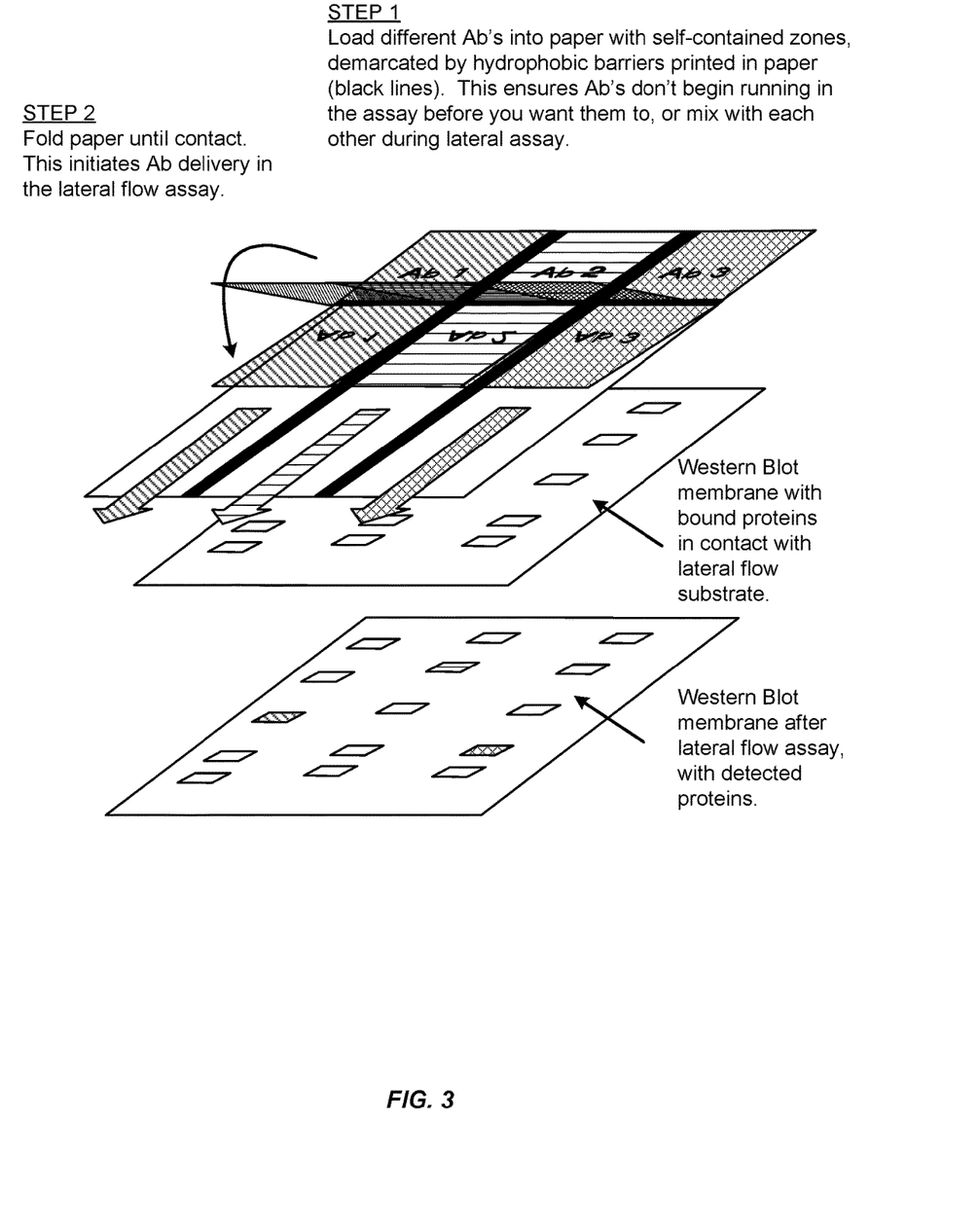
FIG. 3 depicts a method of performing multiplex detection of analytes on a western blot membrane using a porous substrate described herein. A porous substrate is provided and placed in intimate contact with a western blot membrane containing bound proteins (analytes).

An exemplary embodiment is depicted in FIG. 3. FIG. 3 depicts multiplex detection of three different analytes using compositions and methods described herein. In FIG. 3, step 1, three different binding reagents (e.g., antibodies) are loaded onto three different reagent reservoir sub-regions of a porous substrate. The reagent reservoir sub-regions are separated from each other and from the lateral flow region by hydrophobic or impermeable barriers. The porous substrate can be placed in intimate contact with a membrane containing bound (e.g., irreversibly bound) analytes before or after the loading step. In step 2, the reagent reservoir region is contacted with the lateral flow region to initiate lateral flow by, e.g., folding. Lateral flow of the binding reagents in their corresponding lateral flow sub-regions thus allows the binding reagents to bind, and thereby detect, membrane-bound analytes. Thus, in this embodiment, at least three different membrane-bound analytes can be detected simultaneously.

A membrane containing one or more irreversibly bound analyte(s) can be placed in intimate contact with a porous substrate, such as a porous substrate having a lateral flow region. Subsequently initiating flow of one or more binding reagents through the porous substrate can then contact the binding reagent(s) to the membrane-bound analyte(s). In some embodiments, the initiating of lateral flow of binding reagent(s) through the porous substrate is performed by contacting the porous substrate, or contacting the lateral flow region of the porous substrate, or a portion thereof, with a reagent reservoir region, or portion thereof The membrane and/or the lateral flow region can be blocked with a blocking agent before initiating lateral flow of the binding reagent. In some cases, the blocking is performed before placing the membrane in intimate contact with the porous substrate. Alternatively, the blocking is performed after placing the membrane in intimate contact with the porous substrate. Blocking agents are well known in the art and can be used to reduce or eliminate non-specific binding of one or more binding reagents (e.g., one or more primary or secondary binding reagents). Exemplary blocking agents include, without limitation, bovine serum albumin (BSA), methylated BSA, casein, nonfat dry milk, serum, gelatin, or a protein free blocking solution. Exemplary protein free blocking solutions include solutions containing hydrophilic or amphiphilic synthetic polymers.

The lateral flow region and the reagent reservoir region of the porous substrate can be separated by a folding region. In some cases, the contacting of the reagent reservoir region to the lateral flow region is performed by folding the porous substrate at the folding region. Folding the porous substrate at the folding region can contact at least a portion of the reagent reservoir region to at least a portion of the lateral flow region and thus initiate lateral flow of one or more binding reagents from the reagent reservoir region and through the lateral flow region.

The reagent reservoir region can be integral to the porous substrate. Alternatively, the reagent reservoir region can be distinct from, but attached to, the porous substrate (e.g., attached to the lateral flow region of the porous substrate). In still other cases, the reagent reservoir region can be a second porous substrate that is contacted with a first porous substrate in intimate contact with the membrane. In some embodiments, the reagent reservoir region contains multiple reagent reservoir sub-regions. In some cases, the reagent reservoir sub-regions can contain different binding reagents.

The reagent reservoir can contain an aqueous solution containing binding reagent(s). For example, the porous substrate can be provided with binding reagents dried thereon, the binding reagents reconstituted with an aqueous buffered solution, and then used as described herein to detect one or more analytes. The reconstitution can be performed before or after placing the porous substrate in intimate contact with the membrane. Alternatively, the porous substrate can be provided with an aqueous solution containing binding reagents and used as described herein. As yet another alternative, the binding reagents can be applied by the end-user as a solution to the reagent reservoir region, optionally dried and then reconstituted, and then used as described herein.

In some embodiments, upon contacting the reagent reservoir region to the lateral flow region, a binding reagent, or portion thereof, (e.g., a solution containing a binding reagent, or a portion thereof) is wicked away from the reagent reservoir region and through the lateral flow region. In some cases, the contacting causes the binding reagent, or portion thereof to be wicked away from the reagent reservoir region, through the lateral flow region, and into a liquid sink.

The method can include one or more blocking, washing, or secondary detection steps. In some cases, one or more blocking, washing, or secondary detection steps is performed by sequential lateral flow. Sequential lateral flow refers to performing multiple lateral flow steps in a single porous substrate. For example, a porous substrate can be placed in intimate contact with a membrane containing one or more irreversibly bound analytes. Optionally, lateral flow of a wash and/or blocking solution through the porous substrate can then be initiated. Alternatively, or additionally, the membrane can be washed and/or blocked prior to being placed in intimate contact with the porous substrate. Lateral flow of one or more primary binding reagents through the porous substrate (e.g., through a lateral flow region therein) can be initiated, thereby contacting the binding reagent to the irreversibly bound analyte(s). Lateral flow of a wash and/or blocking solution through the porous substrate can then be initiated. In some cases, the wash solution can remove excess or unbound binding reagent. Lateral flow of one or more secondary binding reagents can then be initiated. Excess or unbound secondary binding reagents can be removed by a subsequent blocking or washing step (e.g., by sequential lateral flow).

Sequential lateral flow can be performed with an active device that employs one or more pumps, valves or motors. Alternatively, sequential lateral flow can be performed with a passive device that does not utilize a pump, a valve, a motor, or require an electrical power source. Exemplary passive sequential lateral flow devices are described in U.S. Patent Application Nos. 2010/0239459 and 2013/0164193.

In some cases, one or more blocking or washing steps is performed by pouring, pipetting, or spraying a blocking or washing solution onto the porous substrate. Alternatively, the porous substrate can be soaked in a blocking or washing solution. The pouring, pipetting, spraying or soaking can be performed manually or using an automated device.

In some embodiments, after contacting one or more primary binding reagents (e.g., one or more primary antibodies) to the membrane by lateral flow through the porous substrate, the porous substrate can be removed and one or more, or all, subsequent blocking, washing, or secondary detection steps performed on the membrane.

One or more irreversibly bound analytes can be detected on the membrane by detecting a bound primary or secondary binding reagent (e.g., detecting a labeled primary or secondary antibody). Methods for detecting primary or secondary binding reagents bound to membrane-bound analytes are well known in the art.

Porous substrates can be stored for a period of time before use. For example the porous substrate can be stored for at least about a day, three days, 7-10 days, at least about a month, two months, 3 months, six months, a year or longer, e.g., at about 4, 5, 6, 7, 8, 10, 12, 14, 16, 18, 20, 22, 25, 30, 35, or 37° C. or more. In some cases, the porous substrate is stored with one or more binding reagents therein/on. The binding reagents can be stored in or on the porous substrate dry, substantially dry, or wet. In some cases, the porous substrate or a portion thereof (e.g., the reagent reservoir region) is reconstituted before use.

V. Kits

Kits for performing any of the foregoing methods are described herein. Also described herein are kits containing one or more of the foregoing compositions. In some embodiments, the kit contains one or more (e.g., 1, 2, 3, 4, 5, 6, 7, 8, 9, 10, or more) porous substrates. In some embodiments, the kit contains one or more binding reagents (e.g., one or more primary and/or secondary binding reagents). In some cases, kit contains one or more porous substrates with one or more binding reagents reversibly bound therein. In some cases, the binding reagent(s) are dried onto the porous substrate, or a portion thereof (e.g., dried onto a reservoir region or sub-region). In some cases, the binding reagents are dried onto the porous substrate or portion thereof in the presence of one or more protein aggregation modifying agents. In some cases, the binding reagent(s) are provided as a reagent to be applied to the porous substrate by the end-user.

In some embodiments, the kit contains a cyclodextrin or other protein aggregation modifying agent. In some cases the kit contains one or more of the foregoing porous substrates impregnated with a protein aggregation modifying agent. In some embodiments, the kit contains a protein aggregation modifying agent that can be applied to a porous substrate, or a portion thereof, by the end-user. The protein aggregation modifying agent of the kit can, for example, be provided as a solid (e.g., a powder) or in liquid form (e.g., as a solution). In some cases, the kit contains a protein aggregation modifying agent that can be applied to a porous substrate (e.g., as part of an aqueous solution), or a portion thereof, by the end-user during reconstitution of one or more reversibly bound binding reagents.

VI. Examples

Hydrophobic barriers (e.g., wax barriers) are printed on a porous substrate (e.g., Whatman chromatography paper). The hydrophobic barriers separate a binding reagent reservoir region from a lateral flow region. Hydrophobic barriers also separate reagent reservoir sub-regions. Similarly, hydrophobic barriers separate lateral flow sub-regions. Binding reagents (e.g., antibodies) are loaded onto one, two or three reagent reservoir sub-regions. The hydrophobic barriers block flow between the reagent reservoir and the lateral flow regions, between reagent reservoir sub-regions and between lateral flow sub-regions. See, FIG. 1.

The porous substrate is placed in intimate contact with a western blot membrane containing bound proteins. Folding the porous substrate at the folding region to contact the reagent reservoir region to the lateral flow region initiates lateral flow of the binding reagents through the lateral flow sub-regions. Binding reagents in each lateral flow sub-region do not mix during lateral flow due to the hydrophobic barriers. See, FIG. 2. Thus, each sub-region can independently detect one or more analytes, enabling multiplex detection of analytes bound to a membrane. See, FIG. 3.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A porous substrate having a length and a width and comprising a reagent reservoir region and a lateral flow region, said reagent reservoir region comprising or bordered by an impermeable or hydrophobic barrier, said impermeable or hydrophobic barrier substantially blocking flow of a liquid from the reagent reservoir region into the lateral flow region until lateral flow is initiated, wherein said reagent reservoir region comprises at least a first reagent reservoir sub-region and a second reagent reservoir sub-region, wherein the first and second reagent reservoir sub-regions are not in fluid communication and are separated by a hydrophobic or impermeable barrier that is parallel relative to flow direction; and said lateral flow region comprises at least a first lateral flow sub-region and a second lateral flow sub-region, wherein said first and second lateral flow sub-regions are not in fluid communication and are separated by a hydrophobic or impermeable barrier that is parallel relative to flow direction, wherein the first reagent reservoir sub-region is configured to deliver reagents therein to the first lateral flow sub-region and the second lateral flow sub-region is configured to deliver reagents therein to the second reagent reservoir sub-region.

2. The porous substrate of claim 1, wherein the porous substrate further comprises a folding region, the folding region positioned to allow initiating of lateral flow by folding the porous substrate at the folding region, wherein folding the porous substrate at the folding region contacts at least a portion of the reagent reservoir region to at least a portion of the lateral flow region.

3. The porous substrate of claim 1, wherein the lateral flow region comprises a capillary flow matrix.

4. The porous substrate of claim 1, wherein the reagent reservoir region comprises a capillary flow matrix.

5. The porous substrate of claim 3, wherein at least a portion of the capillary flow matrix is coupled to an impermeable or hydrophobic backing.

6. The porous substrate of claim 4, wherein at least a portion of the capillary flow matrix is coupled to an impermeable or hydrophobic backing.

7. The porous substrate of claim 2, wherein the lateral flow region is configured to wick one or more binding reagents from the reagent reservoir and along the length of the lateral flow region after folding the folding region.

8. The porous substrate of claim 1, wherein at least a portion of the porous substrate is compressible.

9. The porous substrate of claim 1, wherein the reagent reservoir region comprises a first primary binding reagent.

10. The porous substrate of claim 9, wherein the reagent reservoir region further comprises a second primary binding reagent, wherein the first and second primary binding reagents of the reagent reservoir region are separated by an impermeable or hydrophobic barrier.

11. The porous substrate of claim 1, wherein the reagent reservoir region or the lateral flow region comprises a protein aggregation modifying agent.

12. A method for performing a lateral flow assay comprising:

providing the porous substrate of claim 1;

placing the porous substrate in intimate contact with a membrane comprising a plurality of immobilized analytes; and contacting at least one of the lateral flow subregions with at least one of the reagent reservoir subregions, wherein the reagent reservoir subregion comprises a primary binding reagent, thereby causing the primary binding reagent to wick into the lateral flow subregion, and contacting the primary binding reagent to the membrane comprising a plurality of immobilized analytes.

13. A kit comprising the porous substrates of claim 1.

14. The kit of claim 13 further comprising a first and a second primary binding reagent.

15. The kit of claim 13, the kit further comprising a container having a protein aggregation modifying agent.

16. The kit of claim 15, wherein the protein aggregation modifying agent is a cyclodextrin.

17. The porous substrate of claim 1, wherein the hydrophobic or impermeable barriers are printed onto the porous substrate.

18. The porous substrate of claim 17, wherein the hydrophobic or impermeable barriers are wax barriers.

* * * * *

UNITED STATES PATENT AND TRADEMARK OFFICE
CERTIFICATE OF CORRECTION

| | | |
|---|---|---|
| PATENT NO. | : 9,671,402 B2 | Page 1 of 1 |
| APPLICATION NO. | : 14/634209 | |
| DATED | : June 6, 2017 | |
| INVENTOR(S) | : Clayton McKee | |

It is certified that error appears in the above-identified patent and that said Letters Patent is hereby corrected as shown below:

In the Claims

In Column 26, Lines 18-20, Claim 1 should read "second reagent reservoir sub-region is configured to deliver reagents therein to the second lateral flow sub-region."

Signed and Sealed this
Third Day of October, 2017

Joseph Matal
*Performing the Functions and Duties of the*
*Under Secretary of Commerce for Intellectual Property and*
*Director of the United States Patent and Trademark Office*